United States Patent [19]

Stockel

[11] Patent Number: 5,637,681

[45] Date of Patent: Jun. 10, 1997

[54] AMINOSACCHARIDE BIGUANIDES

[76] Inventor: Richard F. Stockel, 475 Rolling Hills Rd., Bridgewater, N.J. 08807

[21] Appl. No.: 583,192

[22] Filed: Jan. 4, 1996

Related U.S. Application Data

[63] Continuation-in-part of Ser. No. 369,735, Jan. 6, 1995, abandoned, which is a continuation-in-part of Ser. No. 131,116, Oct. 4, 1993, abandoned, which is a continuation-in-part of Ser. No. 932,084, Aug. 19, 1992, abandoned.

[51] Int. Cl.$^6$ .................................................. C08B 37/08
[52] U.S. Cl. .................................................. 536/20; 536/18.7
[58] Field of Search .................................................. 536/18.7, 20

[56] References Cited

U.S. PATENT DOCUMENTS 4,373,096  2/1983  Koshugi .................................................. 536/20

FOREIGN PATENT DOCUMENTS

| | | |
|---|---|---|
| 1122209 | 4/1982 | Canada . |
| 0018131 | 10/1980 | European Pat. Off. . |
| 0028126 | 5/1981 | European Pat. Off. . |
| 60-233102 | 11/1985 | Japan . |
| 0729197 | 4/1980 | U.S.S.R. . |

*Primary Examiner*—Kathleen K. Fonda
*Attorney, Agent, or Firm*—Jack Matalon

[57] ABSTRACT

Novel aminosaccharide biguanides are prepared by either reacting a aminosaccharide with a mono- or multi-functional cyanoguanidine or by reacting a monocyano-guanidine of an aminosaccharide with a mono- or multi-functional primary and/or secondary amine. The amines may be straight or branched chain alkyl, aryl, alkaryl, aralkyl, acylic, alicyclic, heterocyclic or polycyclic in nature. The aminosaccharide biguanides have a variety of uses such as for anti-microbial compositions, chelating compositions, cosmetic compositions, surface tension reductants, flocculants for flocculating negatively charged suspended particles, and the like.

6 Claims, No Drawings

AMINOSACCHARIDE BIGUANIDES

RELATED APPLICATIONS

This application is a continuation-in-part of my application, Ser. No. 08/369,735 filed Jan. 6, 1995, now abandoned, which was a continuation-in-part of my application, Ser. No. 08/131,116 filed Oct. 4, 1993, now abandoned, which in turn was a continuation-in-part of my application Ser. No. 07/932,084 filed Aug. 19, 1992, now abandoned.

FIELD OF THE INVENTION

The invention relates to novel aminosaccharide biguanides. For the purposes of the invention, the term "aminosaccharide" is to be understood as encompassing monomeric, dimeric, trimeric, oligomeric and polymeric aminosaccharides having an amino functionality attached in the 2-, 3-, or 6-carbon position of the saccharide moiety. Specific nonlimiting examples of suitable aminosaccharides include 2-amino-2-deoxy-D-glucopyranose, 2-amino-2-deoxy-D-galactopyranose, glycosaminoglycans such as chitosan, and other polysaccharides having a D-glucose amino-containing unit such as hyaluronic acid or deacylated hyaluronic acid.

The aminosaccharide biguanides of the invention exhibit useful properties such as anti-microbial activity, chelating capability, emollient properties useful for cosmetic compositions, surface tension reduction, capability of flocculating negatively charged suspended particles and the like.

BACKGROUND OF THE INVENTION

The prior art literature is replete with examples of aminosaccharide derivatives. U.S. Pat. Nos. 3,879,376 and 3,953,608 disclose the reaction of saturated or unsaturated diacid anhydrides so as to produce acylated derivatives.

Amine-containing polysaccharides, including monoaminosaccharide, may be reductively alkylated with various aldehyde or keto compounds to convert the amine group via a covalent bond to a =CH— or —CH$_2$— linkage as disclosed in U.S. Pat. No. 4,424,346. U.S. Pat. No. 4,619,995 is directed to the preparation of aminosaccharide derivatives in which carboxymethyl substituents are introduced on some of the amino and hydroxy sites of the aminosaccharide units.

Quaternary hydroxyalkyl-substituted aminosaccharide derivatives useful as cosmetic compositions are disclosed in U.S. Pat. Nos. 4,772,689, 4,822,598, 4,835,266 and 4,976,952. U.S. Pat. No. 4,957,908 discloses the preparation of aminosaccharide pyrithione and states that such compound possesses anti-microbial activity.

European Patent 0400364 describes the preparation of aminosaccharide derivatives wherein the amino groups are converted to quaternary ammonium salts. Dithiocarbamates of aminosaccharide, claimed to be effective chelating agents, are disclosed in *Carbohydrate Research*, 104, (1982) 235–243. A wide variety of aminosaccharide derivatives and their potential application applications are described in *Carbohydrate Polymers*, 3, (1983) 53–75.

Despite the voluminous literature describing a wide array of aminosaccharide derivatives, there appears to be only one prior art reference which bears any relevance to the present invention. Japanese Kokai 60233102 discloses the preparation of an aminosaccharide biguanide acid salt by reacting monoaminosaccharide with dicyandiamide. However, the structure and properties of the resultant aminosaccharide biguanide acid salt differ markedly from the structures and properties of the aminosaccharide biguanides of the present invention. In particular, the aminosaccharide biguanides of the present invention possess properties not mentioned in any prior art teachings as being associated with aminosaccharide derivatives.

SUMMARY OF THE INVENTION

In accordance with the invention, novel aminosaccharide biguanides having unique structures and properties are prepared by reaction of the aminosaccharide with a cyanoguanidine or by reaction of the cyanoguanidine derivative of the aminosaccharide with a primary and/or secondary amine. These reactions may be readily carried out in aqueous media in the presence of a protonating agent, e.g. HCl. Organic solvents, i.e. aprotic dipolar solvents such as dimethylformamide, dimethyl sulfoxide or N-methylpyrrolidone, may be used in place of, or in addition to water.

U.S. Pat. No. 5,442,048 teaches a method to activate chitosan such that the reactions can be carried out using small reaction volumes concurrent with higher degrees of substitution on the nitrogen atom of the amino group. The process involves dispersing chitosan in the presence of either inorganic or organic suspending agents by first forming the acid salt, e.g. the hydrochloride salt. This is followed by adding base, e.g. sodium hydroxide, yielding an activated suspension of chitosan in an aqueous medium with a pH of about 10.0. The activated chitosan is then thoroughly washed with water to remove all contaminants. The activated chitosan results in higher degrees of substitution upon derivatization. This unique procedure is quite useful for preparation of the aminosaccharide biguanides of the invention.

Alternatively, the reactions for preparing the aminosaccharide biguanides of the invention may be carried out under autogenous pressures at elevated temperatures in a pressure vessel using water or a combination of water-soluble co-solvents. More recently, *Polymer*, 24, no. 5, (1993) 1102, describes the use of supercritical fluids for the chemical modification of monoaminosaccharide. Such alternative methods are clearly within the purview of the present invention for the purpose of preparing the aminosaccharide biguanides having the structures described and claimed hereinbelow.

Most aminosaccharide derivatives have limited water solubility, thereby limiting their commercial usefulness. By contrast, the aminosaccharide biguanides of the invention are quite soluble in water. Indeed, the aminosaccharide biguanides of the invention are capable of forming micellar solutions with concentrations of 25 wt. % or even higher.

The aminosaccharide biguanides of the invention also possess unique surface tension-reducing properties, especially when the aminosaccharide biguanides are formed by having ethylene oxide and/or propylene oxide units present in the cyanoguanidine reactant. The aminosaccharide biguanides of the invention also possess numerous other commercially useful properties, e.g. chelating capability, a high degree of adherence to formal negative charges present in various materials such as skin, hair, paper, suspended particles in water, etc. Moreover, the aminosaccharide biguanides of the invention have the capability of enhancing the viscosity of aqueous solutions. In addition, those aminosaccharide biguanides of the invention containing ethylene oxide and/or propylene oxide functionalities have properties suitable for cosmetic compositions, because they act as emollients and enhance penetration of the skin.

The aminosaccharide biguanides of the invention may be readily prepared by the reactions below wherein chitosan is utilized as the aminosaccharide for illustrative purposes. In Reaction 1 (which is preferred), chitosan and the desired cyanoguanidine are reacted in the presence of aqueous acidic media, e.g. HCl. The cyanoguanidine reactant may be readily prepared by reacting the desired primary or secondary amine with sodium dicyanamide in water and/or an organic solvent. Primary amines are preferred. However, the amine need not be a monoamine; diamines, triamines, tetramines, pentamines, hexamines, etc. may be used to produce the desired cyanoguanidine.

REACTION 1

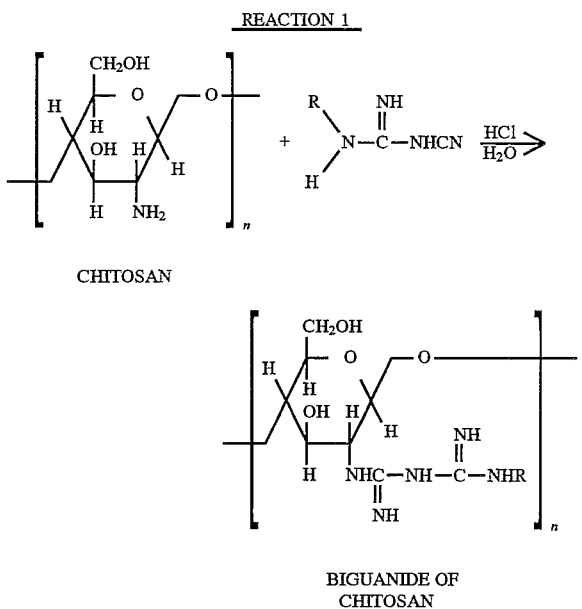

CHITOSAN

BIGUANIDE OF CHITOSAN

A particularly effective method of preparing the aminosaccharide biguanides of the invention involves carrying out the reaction in a pressure vessel at a temperature in the range of 125°–160° C. to assure a significant conversion within a relatively short time frame of 2–6 hours, rather than the more lengthy reaction time of greater than 6 hours if the reaction is conducted at a lower temperature, e.g. 100° C. The pressure will range from about 25 to about 300 psi depending on the solvent system used in the reaction.

In Reaction 2, the monocyanoguanidine of chitosan is reacted with the appropriate mono- or higher primary or secondary amine, again in the presence of an aqueous acidic media such as HCl. The chitosan monocyanoguanidine in turn may be readily prepared by reacting chitosan with sodium dicyanamide in water and/or an organic solvent.

REACTION 2

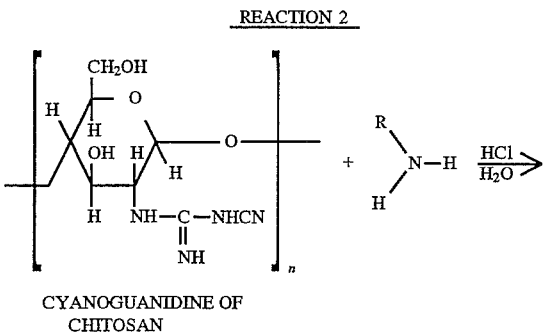

CYANOGUANIDINE OF CHITOSAN

-continued
REACTION 2

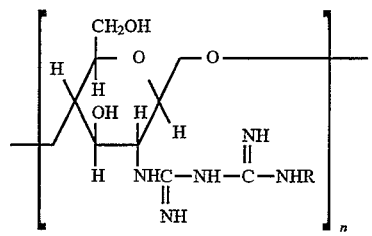

BIGUANIDE OF CHITOSAN

Any relatively pure grade of a aminosaccharide may be used, provided that it has a reasonable degree of deacetylation, preferably at least 50%.

A wide variety of amines may be used to prepare the aminosaccharide biguanides of the present invention. The amines will possess one or more primary (preferred) or secondary amino groups and may be alkyl, aryl, aralkyl, alkaryl, acyclic, alicyclic, heterocyclic, or polycyclic (bi-, tri- or multi-cyclic) in nature and may contain from 2 to about 200 total carbon atoms. The amines may be substituted or unsubstituted and may possess branched and/or straight chains. If substituted, the substituents should be such as to not unduly compete with the reaction employed to prepare the reactants or with Reaction 1 or Reaction 2.

DETAILS OF THE INVENTION

The invention relates to the preparation of biguanides of an aminosaccharide; the aminosaccharide starting material will preferably have at least 50% of its amino groups in a free form, i.e. deacylated. The viscosity of the aminosaccharide is not critical; all that is necessary is that the viscosity in the chosen aqueous and/or organic diluent be sufficiently low to allow thorough mixing of the reactants in order to achieve high conversion rates.

When preparing the aminosaccharide biguanides, an acid must be present during the reaction in order to protonate all of the free amino groups present in the aminosaccharide which are capable of participating in the reaction. It is the protonated form of the free amino group which adds to the triple bond of the cyano group present in the chosen cyanoguanidine reactant. Any acid which has the capability of protonating free amino groups such that the resultant aminosaccharide biguanide salts will be soluble in water may be used, e.g. hydrochloric, nitric, formic, acetic, propionic, gluconic, lactic, citric, malonic, malic, pyruvic, succinic, adipic, etc.

As mentioned above, a wide variety of primary or secondary amines may be used to prepare the aminosaccharide biguanides of the invention. Primary amines are preferred because they generally result in higher yields. The amines may be unsubstituted or they may contain substituents which will not competitively react under the reaction conditions employed in preparing the reactants or in Reaction 1 or Reaction 2. Nonlimiting examples of suitable substituent functionalities include double bonds, alkyl, aryl, aralkyl and alkaryl groups, halo, nitro, hydroxyl, amido, tertiary amino, carboxylic, etc.

The hydrocarbyl moieties of the amines may be interrupted with 0 to about 100 oxygen atoms, 0 to 6 divalent, trivalent or tetravalent sulfur atoms or 0 to 8 tertiary nitrogen atoms. Nonlimiting examples of such amines are $H_2N(CH_2)_6CH_3$, $H_2N(CH_2)_4OH$, $H_2N(CH_2)_2Cl$, $H_2N(CH_2)_3SO_2CH_3$, $CH_3NH(CH_2)_2CH_3$, $H_2NCH_2CH=CH_2$, as well as the following:

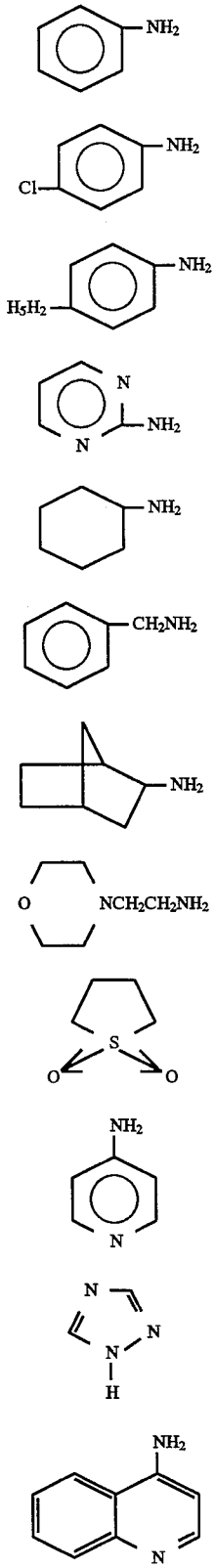

-continued

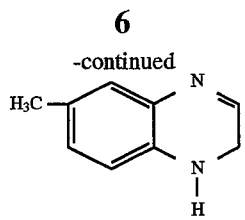

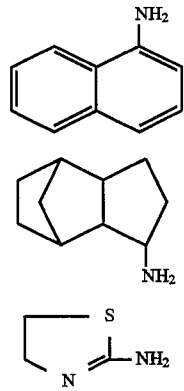

Aminosaccharide biguanides with desirable surface activity properties may be readily prepared by the processes described above by employing amines containing alkylene oxide functionalities, e.g. ethylene oxide and/or propylene oxide units, within the amine molecule. Examples of such amines are as follows:

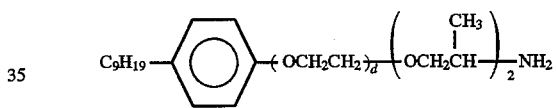

wherein d is an integer of 1 to about 15 and

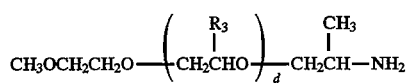

wherein $R_3$ is methyl or hydrogen

In the structures shown immediately above, the molar ratio of ethylene oxide units will typically range from 0 to about 31, while the molar ratio of propylene oxide units will typically range from about 3 to about 32. The alkylene oxide-substituted amines are commercially available, e.g. from Texaco Chemical Co. These amines confer very useful surface active properties to the aminosaccharide biguanides of the present invention with the result that they may be used for a variety of cosmetic applications, e.g. as hair conditioning agents inasmuch as such aminosaccharide biguanides are cationic in nature and will therefore readily interact with the anionic groups present in human hair.

Other useful types of alkylene oxide-substituted amines for preparing the present aminosaccharide biguanides are embraced by the following structures:

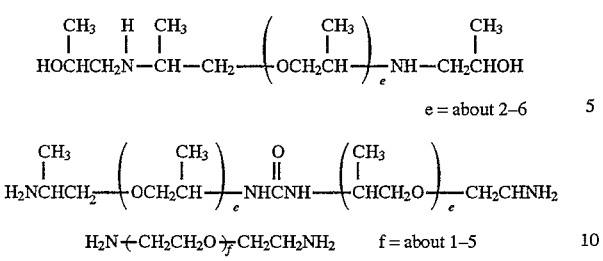

e = about 2–6

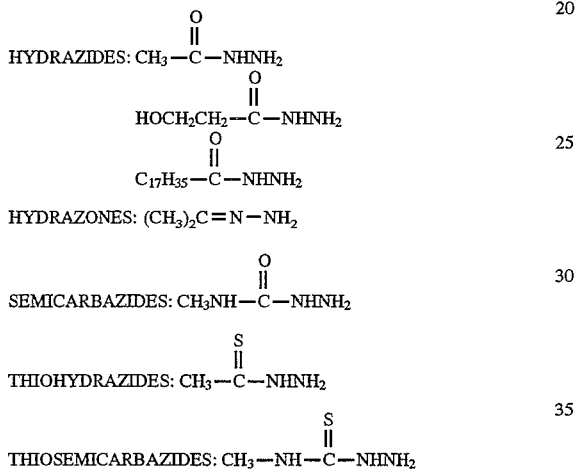

f = about 1–5

In addition to the alkylene oxide substituted amines described above, another group of amino compounds which are useful for conversion to monocyano derivatives containing diverse functionalities are the following:

HYDROXYAMINES: $NH_2OH$

HYDRAZIDES: $CH_3-\overset{O}{\underset{\|}{C}}-NHNH_2$ $HOCH_2CH_2-\overset{O}{\underset{\|}{C}}-NHNH_2$ $C_{17}H_{35}-\overset{O}{\underset{\|}{C}}-NHNH_2$

HYDRAZONES: $(CH_3)_2C=N-NH_2$

SEMICARBAZIDES: $CH_3NH-\overset{O}{\underset{\|}{C}}-NHNH_2$

THIOHYDRAZIDES: $CH_3-\overset{S}{\underset{\|}{C}}-NHNH_2$

THIOSEMICARBAZIDES: $CH_3-NH-\overset{S}{\underset{\|}{C}}-NHNH_2$

In addition to the monoamines described above, there are numerous types of diamines which may be employed in the preparation of the present aminosaccharide biguanides. Nonlimiting examples of suitable diamines include the following:

$H_2N(CH_2)_2-N(CH_3)-(CH_2)_2NH_2$ $H_2NCH_2CH_2OCH_2CH_2NH_2$ $H_2N(CH_2)_3SO_2(CH_2)_3NH_2$ $H_2N(CH_2CH_2O)_3CH_2CH_2NH_2$ $HN(CH_3)-CH_2CH_2-NHCH_3$ $H_2N-CH_2-CH(OH)-CH_2-NH_2$ $\begin{array}{c} H_2N-CH-COOH \\ | \\ H_2N-CH-COOH \end{array}$

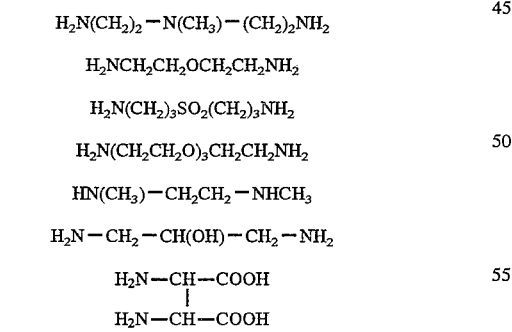

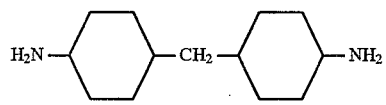

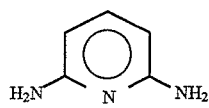

Other examples of diamines useful for preparing the present aminosaccharide biguanides are the following diamino hydrazines, hydrazides, hydrazones, tricarbohydrazides and carbohydrazides:

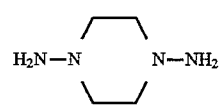

-continued $$H_2NN=CH-(CHOH)_4-CH=NNH_2$$

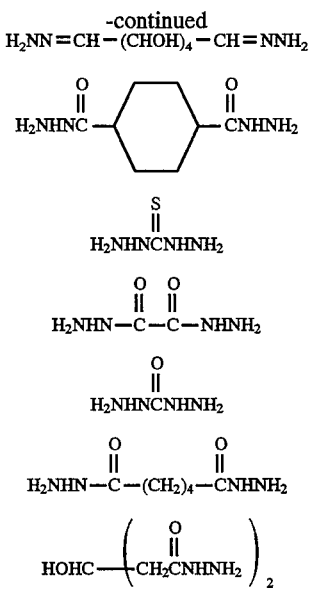

$$H_2NHNCNHNH_2 \atop \|\atop S$$

$$H_2NHN-\underset{\|}{\overset{O}{C}}-\underset{\|}{\overset{O}{C}}-NHNH_2$$

$$H_2NHNCNHNH_2 \atop \|\atop O$$

$$H_2NHN-\underset{\|}{\overset{O}{C}}-(CH_2)_4-\underset{\|}{\overset{O}{C}}NHNH_2$$

$$\left(HOHC-\left[CH_2\underset{\|}{\overset{O}{C}}NHNH_2\right]\right)_2$$

Triamino reactants may also be employed to form the corresponding tricyano derivatives. Although there are far fewer commercially available triamino compounds and even though the economics may not be favorable, the triamino compounds are also quite useful for preparing the present aminosaccharide biguanides. Nonlimiting examples of useful triamino compounds are as follows:

$$HOC(CH_2NH_2)_3$$

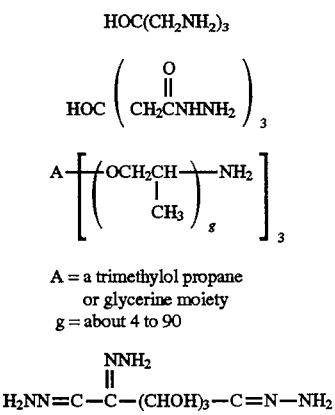

A = a trimethylol propane
or glycerine moiety
g = about 4 to 90

$$H_2NN=C-\underset{\|}{\overset{NNH_2}{C}}-(CHOH)_3-C=N-NH_2$$

As mentioned above, the invention is not dependant on the number of amino groups in the compounds used to prepare the aminosaccharide biguanides. Thus, although they are rare and expensive, compounds with tetra-, penta- and hexa-amino functionalities are quite useful for preparing the present aminosaccharide biguanides.

THE AMINOSACCHARIDE BIGUANIDES

The aminosaccharide biguanides of the invention will have the amino group present in the 2-, 3- or 6- position and, in the form of their free bases, have a structure selected from the group consisting of I, II, III and IV:

$$\text{(aminosaccharide)}_n-NH-\underset{\|}{\overset{NH}{C}}-NH\underset{\|}{\overset{NH}{C}}-N\underset{R_1}{\overset{X}{\diagup}} \qquad \text{I}$$

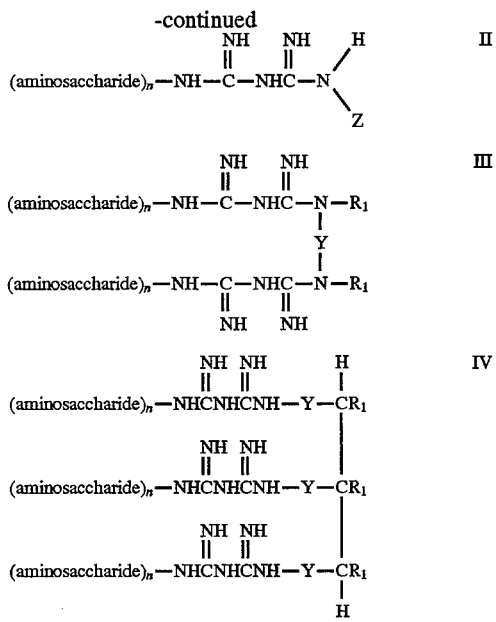

wherein n is an integer having a value of 1 to about 7,000; X is a hydrocarbyl moiety containing 7 to about 200 carbon atoms and Y is a hydrocarbyl moiety containing 1 to about 200 carbon atoms wherein the carbon atoms within the X and Y moieties are independently interrupted with atoms selected from the group consisting of: (a) 0 to about 100 oxygen atoms, (b) 0 to 6 divalent, trivalent or tetravalent sulfur atoms and (c) 0 to 8 tertiary nitrogen atoms; and Z is a moiety selected from the group consisting of $-NR_1OH$, $-NH-NR_1R_2$, $-NH-NH-CMNR_1R_2$, $-NH-N=CR_1R_2$, $-NH-CM-NH-NR_1R_2$ and $-NH-NH-CMNR_1R_2$, wherein M is oxygen or sulfur, R is a straight or branched chain alkyl, aryl, alkaryl, aralkyl, acyclic, alicyclic, heterocyclic or polycyclic having up to 18 carbon atoms, and $R_1$ and $R_2$ are independently hydrogen or the same or different straight or branched chain alkyl, aryl, alkaryl, aralkyl, acylic, alicyclic, heterocyclic or polycyclic groups having up to 18 carbon atoms.

For the purposes of this invention, the aminosaccharide biguanides may also be present in their salt forms wherein the anion is selected from the group consisting of chloride, bromide, iodide, nitrate, formate, acetate, propionate, malate, lactate, citrate, glycolate, gluconate, sulfonate, sulfate, phosphate, phosphonate, tartrate and oxalate.

Preferably, the X and Y moieties are each independently interrupted with 1 to 8 tertiary nitrogen atoms and are derived from an amine selected from the group of acyclic amines, alicyclic amines, aryl amines, alkaryl amines, aralkyl amines, heterocyclic amines and polycyclic amines.

Alternatively, the X and Y moieties are each independently interrupted with 1 to about 100 oxygen atoms and comprise at least one polyoxyalkylene radical.

Preferably, the polyoxyalkylene radical is derived from:

(i) an amine-terminated polyalkylene glycol having the structure:

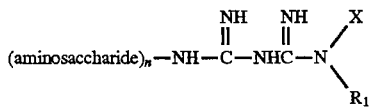

wherein j is an integer having a value of 2 to about 68; or (ii) a polyether diamine having the structure:

$$H_2N-CHCH_2-\left[OCH_2CH-\right]_a-\left[OCH_2CH_2\right]_b-\left[OCH_2CH-\right]_c-NH_2$$
$$\phantom{H_2N-}CH_3 \phantom{-[O}CH_3 \phantom{-[OCH_2CH_2-]}CH_3$$

wherein b has a value of about 8.5 to 131.5, a has a value of 0 to 2.5, c has a value of 0 to 2.5 and the sum of a+c is about 2.5; or (iii) a bis-hydroxypropylaminopolypropylene glycol having the structure:

$$HOCHCH_2-NH-CHCH_2-\left[OCH_2CH-\right]_k-NH-CH_2CHOH$$
$$\phantom{HOC}CH_3 \phantom{-NH-}CH_3 \phantom{-[O}CH_3 \phantom{-NH-CH_2}CH_3$$

wherein k is an integer having a value of about 1 to 6; or (iv) a urea condensate of an amine-terminated polypropylene glycol having the structure:

$$H_2NCHCH_2-\left[OCH_2CH-\right]_q-NHCNH-\left[CHCH_2O-\right]_2-CH_2CHNH_2$$

wherein 1 is an integer having a value of about 1 to 6; or (v) an amine-terminated alkylene glycol having the structure:

$$H_2NCHCH_2-\left[OCH_2CH-\right]_m-OCH_2CHNH_2$$
$$\phantom{H_2NC}R_3 \phantom{-[OC}R_3 \phantom{-OCH_2C}R_3$$

wherein m is an integer having a value of about 0 to 4 and $R_3$ is hydrogen or a methyl group; or (vi) an amine-terminated polyalkylene glycol having the structure:

$$H_2N-\left[CHCH_2O-\right]_s-\left[CH_2-\right]_t-\left[OCH_2CH-\right]_s-NH_2$$
$$\phantom{H_2N-[}R_3 \phantom{HCH_2O-]-[CH_2-]-[OCH_2C}R_3$$

wherein s is an integer having a value of about 1 to 10, t is an integer having a value of about 2 to 12 and $R_3$ is hydrogen or a methyl group.

Unique and very useful aminosaccharide biguanides are obtained wherein the X and Y moieties each independently contain at least one pendant functionality selected from the group consisting of hydroxy, carboxylic, sulfonic and quaternary nitrogen groups.

Another group of useful aminosaccharide biguanides are obtained when the X and Y moieties are each independently interrupted with 1 to 6 sulfur atoms and comprise at least one sulfide, disulfide, sulfoxide or sulfone.

As mentioned above, the aminosaccharide biguanides of the invention will have the amino group present in the 2, or 6 position. Preferably, the amino group will be present in the 2 position as shown below in respect to structure I wherein the aminosaccharide is chosen to be chitosan for illustrative purposes:

$$\left[\begin{array}{c} \text{chitosan-biguanide structure} \\ \text{with } NHC-NH-C-N \\ \phantom{xx} \| \phantom{xxx} \| \phantom{xx} \diagdown \\ \phantom{xx} NH \phantom{xxx} X \phantom{xx} R_1 \end{array}\right]_n$$

wherein X, $R_1$ and n have the same values as set forth above.

Preparation of the Aminosaccharide Biguanides

A major advantage of the invention is the relative simplicity of the reaction conditions. The reactants are added in a molar ratio of 1:1:1 representing aminosaccharide, monocyanoguanidine and protonic acid; 2:1:2 representing aminosaccharide, dicyanoguanidine and protonic acid; 3:1:3 representing aminosaccharide, tri-substituted amine and protonic acid, etc. Conversely, the cyano=guanidine of aminosaccharide may be reacted with an amino compound in the presence of an equivalent amount of protonic acid based on the amount of free amino groups. The reaction is preferably carried out in aqueous solution under reflux conditions for about 6–20 hours. Alternatively, aprotic and aprotic dipolar solvents may be used as the reaction medium in the presence or absence of water. As a further alternate, the reaction may be carried out in water, water-soluble organic solvents or mixtures thereof under autogenous pressure. Still yet another alternate involves the use of a two-phase transfer agent utilizing water and a water-immiscible agent.

General Method for the Preparation of the Aminosaccharide Biguanides

To a suitably-sized reaction vessel is added a measured amount of a aminosaccharide followed by addition of the desired cyanoguanidine such that an equivalent amount of cyanoguanidine is added for every amino group of the aminosaccharide. Thereafter enough distilled water containing a protonic acid capable of reacting with the amino functionality on the aminosaccharide molecule to afford a stirrable reaction mixture is added. The reaction mixture is then refluxed for about 6–20 hours to assure conversion to the aminosaccharide biguanide salt. If the activation energy required for a particular derivative is higher than that obtainable by the reflux temperature of the aqueous medium, a higher temperature can be achieved by operating under pressure. Other synthetic procedures which are feasible include the use of supercritical fluids such as $CO_2$ or the use of phase transfer agents in the presence of two immiscible solvents.

To obtain the aminosaccharide biguanide in a highly purified form, the reaction mixture is added to 1–4 times the volume of an alcohol such as methanol, ethanol, isopropanol, etc. The precipitated polymer is thoroughly dispersed in this water-alcohol mixture and then isolated and dried under vacuum and/or heat. The presence of the desired polymer may be verified by the absence of cyano absorption in the IR spectra at 2200–2300 $cm^{-1}$ and by elemental nitrogen analysis.

Alternatively, the cyanoguanidine derivative of a aminosaccharide is prepared by reaction with sodium dicyanamide and an equimolar amount of hydrochloric acid in an aqueous refluxing medium. The resultant derivative is then reacted with the appropriate amine and acid in the aqueous refluxing medium.

General Procedure for the Preparation of the Cyanoguanidines

The correct molar proportions of an amine, sodium dicyanamide and protonic acid are added to any aqueous medium and the reaction mixture is refluxed for 6–18 hours. Hydroxylic solvents or aprotic dipolar solvents may also be used in place of, or in combination with, the aqueous medium. Other synthetic methods include the use of pressure vessels under autogenous conditions, the use of cosolvents, the use of supercritical fluids as well as the use of two-phase transfer agents with water-immiscible solvents.

Structures of Typical Cyanoguanidines

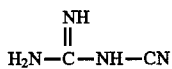

dicyandiamide

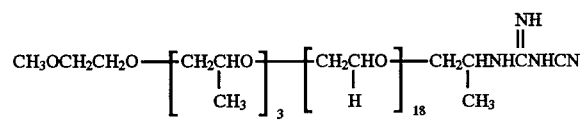

monocyanoguanidine of "JEFFAMINE" M-1000

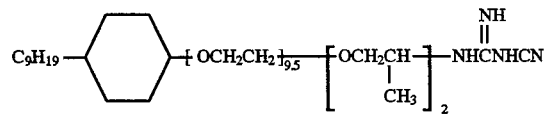

monocyanoguanidine of "SURFONAMINE" MNPA-750

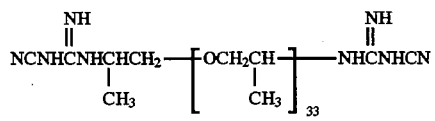

biscyanoguanidine of "JEFFAMINE" D-2000

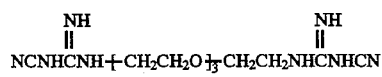

biscyanoguanidine of "JEFFAMINE" 192

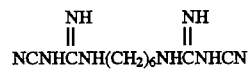

biscyanohexamethylene biguanide

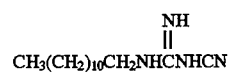

cyanoguanidine of dodecylamine

cyanoguanidine of hydroxylamine

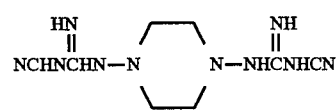

biscyanoguanidine of 1,4-diaminopiperazine

cyanoguanidine of 3-hydroxypropionic hydrazide

-continued
Structures of Typical Cyanoguanidines

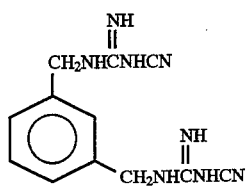

biscyanoguanidine of m-xylylenediamine

Table I below lists the components (and molar amounts) for the production of chitosan biguanides utilizing those cyanoguanidines whose structures are set forth above. Also listed in Table I are the weight % solids of the chitosan biguanides in aqueous solution.

TABLE I

| Sample | Moles | Component | Wt. % Solids |
|---|---|---|---|
| A | 1 | dicyandiamide | 4.6 |
|   | 1 | chitosan |   |
|   | 1 | hydrochloric acid |   |
| B | 1 | monocyanoguanidine of JEFFAMINE ® M-1000 | 11.0 |
|   | 1 | chitosan |   |
|   | 1 | hydrochloric acid |   |
| C | 1 | monocyanoguanidine of SURFONAMINE ® MNPA-750 | 16.4 |
|   | 1 | chitosan |   |
|   | 1 | hydrochloric acid |   |
| D | 1 | monocyanoguanidine of JEFFAMINE ® D-2000 | 20.0 |
|   | 2 | chitosan |   |
|   | 2 | hydrochloric acid |   |
| E | 1 | monocyanoguanidine of JEFFAMINE ® 192 | 8.8 |
|   | 2 | chitosan |   |
|   | 2 | hydrochloric acid |   |
| F | 1 | biscyanoguanidine of 1,6-hexamethylenediamine | 7.6 |
|   | 2 | chitosan |   |
|   | 2 | hydrochloric acid |   |
| G | 1 | biscyanoguanidine of 2-hydroxy-1,3-diaminopropane | 6.0 |
|   | 2 | chitosan |   |
|   | 2 | hydrochloric acid |   |
| H | 1 | tricyanoguanidine of JEFFAMINE ® T-3000 | 24.0 |
|   | 3 | chitosan |   |
|   | 3 | hydrochloric acid |   |
| I | 1 | cyanoguanidine of JEFFAMINE ® M-2005 | 12.0 |
|   | 1 | chitosan |   |
|   | 1 | hydrochloric acid |   |
| J | 0.5 | cyanoguanidine of dodecylamine | 10.5 |
|   | 1 | chitosan |   |
|   | 1 | hydrochloric acid |   |
| K | 1 | cyanoguanidine of hydroxylamine | 13.0 |
|   | 1 | chitosan |   |
|   | 1 | hydrochloric acid |   |
| L | 1 | biscyanoguanidine of 1,4-diaminopiperazine | 15.0 |
|   | 2 | chitosan |   |
|   | 4 | hydrochloric acid |   |
| M | 1 | cyanoguanidine of 3-hydroxypropionic hydrazide | 9.0 |
|   | 1 | chitosan |   |
|   | 1 | hydrochloric acid |   |

TABLE I-continued

| Sample | Moles | Component | Wt. % Solids |
|---|---|---|---|
| N | 1 | biscyanoguanidine of m-xylylenediamine | 7.0 |
|   | 2 | chitosan |   |
|   | 2 | hydrochloric acid |   |

A variety of reaction procedures are possible when reacting an amino substrate with a cyanoguanidine substrate in the presence of a protonic acid. The solvent may be, e.g. water, glycols, alcohols, aprotic dipolar solvents or combinations thereof as well as supercritical carbon dioxide.

The reaction is preferably carried out at a temperature in the range of about 125° to about 160° C. under pressure if necessary depending upon the boiling point of the particular solvent used. Lower temperatures in the range of about 100° to about 125° C. are also acceptable; however, at such lower temperatures, conversion rates tend to be lower and reaction times are much longer, usually in the range of 10–24 hours or more.

Chelating Property of Sample A 0.015 g of Sample A was added to 15 ml of an aqueous solution containing 25 ppm of $Cu(NO_3)_2$ in 500 ml distilled water. After stirring for 1.5 hours, the precipitated $Cu^{+2}$ chitosan biguanide complex was filtered off and the supernatant liquid was measured on a visible spectrophotometer and compared to a set of standards to determine the metal ion concentration remaining in solution. The results indicated a greater than 90% removal efficiency of $Cu^{+2}$ from solution.

Flocculating Capability of Sample F

A 2 wt. % kaolin suspension was prepared using distilled water. The pH was adjusted to about 6.0±0.5 units. The stirred solution was turbid with the kaolin thoroughly dispersed. When a 0.02 wt. % portion of Sample F was dispersed in the kaolin mixture, the solution became clear within a 6 hour period.

Soft Contact Lens Cleaner/Preservative using Sample C

The uniqueness of a aminosaccharide biguanide containing ethylene oxide and/or propylene oxide units is that the hydrophilic-lipophilic balance ("HLB") can be controlled to achieve a micellar solution. This allows the preparation of high solids content solutions having a considerable degree of fluidity with emollient and cleaning properties. Another outstanding property of such aminosaccharide biguanides is the ability to reduce the interfacial surface tension in aqueous solutions. Such property is quite useful for removal of dirt and grit from contact lens surfaces.

A number of references exist in the literature relating to block copolymers containing ethylene oxide and/or propylene oxide units. However, in every case, an anti-microbial agent is added as the active germicidal ingredient. Such teachings can be found in U.S. Pat. Nos. 3,855,140, 3,882,036 and 4,440,662. However, the aminosaccharide biguanides of the invention which contain ethylene oxide and/or propylene oxide units possess both properties of cleaning and anti-microbial activity in a single composition. A typical formulation is as follows:

| | |
|---|---|
| Sample C | 1.0 wt. % |
| NaCl | 0.70 wt. % |
| $Na_3EDTA$ | 0.10 wt. % |
| Distilled Water O.S. | 100.0 wt. % |

The examples set forth above are merely illustrative of the unlimited variety of aminosaccharide biguanides of the present invention. The scope of the invention is limited only by the claims which are appended hereinbelow.

What is claimed is:

1. A biguanide of an aminosaccharide, or salt thereof, having the amino group present in the 2, 3 or 6 position and which, in the form of its free base, has a structure selected from the group consisting of I, II, III and IV:

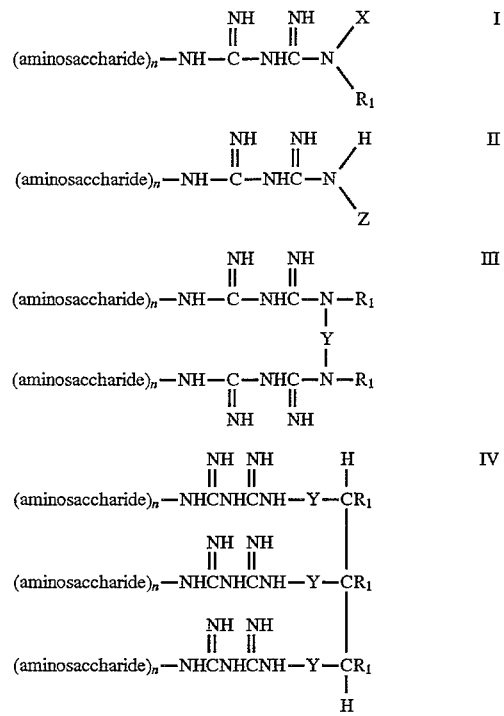

wherein n is an integer having a value of 1 to about 7,000; X is a hydrocarbyl moiety containing 7 to about 200 carbon atoms and Y is a hydrocarbyl moiety containing 1 to about 200 carbon atoms wherein the carbon atoms within the X and Y moieties are independently interrupted with atoms selected from the group consisting of: (a) 0 to about 100 oxygen atoms, (b) 0 to 6 divalent, trivalent or tetravalent sulfur atoms and (c) 0 to 8 tertiary nitrogen atoms; and Z is a moiety selected from the group consisting of —$NR_1OH$, —NH—$NR_1R_2$, —NH—NH—$CMNR_1R_2$, —NH—N=$CR_1R_2$, —NH—CM—NH—$NR_1R_2$ and —NH—NH—$CMNR_1R_2$, wherein M is oxygen or sulfur, R is a straight or branched chain alkyl, aryl, alkaryl, aralkyl, acyclic, alicyclic, heterocyclic or polycyclic having up to 18 carbon atoms, and $R_1$ and $R_2$ are independently hydrogen or the same or different straight or branched chain alkyl, aryl, alkaryl, aralkyl, acylic, alicyclic, heterocyclic or polycyclic groups having up to 18 carbon atoms.

2. The biguanide of claim 1 which is present in its salt form wherein the anion is selected from the group consisting of chloride, bromide, iodide, nitrate, formate, acetate, propionate, malate, lactate, citrate, glycolate, gluconate, sulfonate, sulfate, phosphate, phosphonate, tartrate and oxalate.

3. The biguanide of claim 1 wherein the X and Y moieties are each independently interrupted with 1 to 8 tertiary nitrogen atoms and are derived from an amine selected from the group consisting of acyclic amines, alicyclic amines, aryl amines, alkaryl amines, aralkyl amines, heterocyclic amines and polycyclic amines.

4. The biguanide of claim 1 wherein the X and Y moieties are each independently interrupted with 1 to about 100 oxygen atoms and comprise at least one polyoxyalkylene group.

5. The biguanide of claim 4 wherein the polyoxyalkylene group is selected from the group consisting of:

(i) an amine-terminated polyalkylene glycol having the structure:

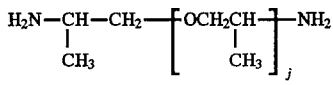

wherein j is an integer having a value of 2 to about 68; or (ii) a polyether diamine having the structure:

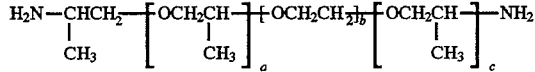

wherein b has a value of about 8.5 to 131.5, a has a value of 0 to 2.5, c has a value of 0 to 2.5 and the sum of a+c is about 2.5; or (iii) a bis-hydroxypropylaminopolypropylene glycol having the structure:

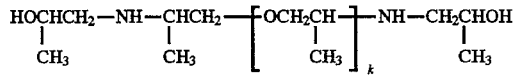

wherein k is an integer having a value of about 1 to 6; or (iv) a urea condensate of an amine-terminated polypropylene glycol having the structure:

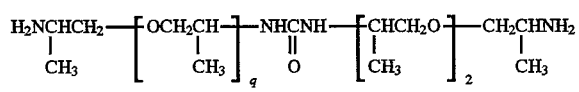

wherein l is an integer having a value of about 1 to 6; or (v) an amine-terminated alkylene glycol having the structure:

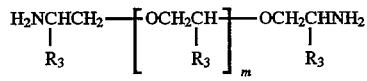

wherein m is an integer having a value of about 0 to 4 and $R_3$ is hydrogen or a methyl group; or (vi) an amine-terminated polyalkylene glycol having the structure:

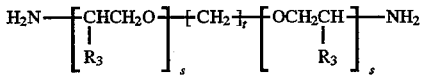

wherein s is an integer having a value of about 1 to 10, t is an integer having a value of about 2 to 12 and $R_3$ is hydrogen or a methyl group.

6. The biguanide of claim 1 wherein the X and Y moieties are each independently interrupted with 1 to 6 sulfur atoms and comprise at least one sulfide, disulfide, sulfoxide or sulfone.

* * * * *